US005607838A

United States Patent [19]

Hattori et al.

[11] Patent Number: 5,607,838
[45] Date of Patent: Mar. 4, 1997

[54] METHOD FOR DETERMINATION OF α-AMYLASE ACTIVITY

[75] Inventors: Shizuo Hattori; Yoshihiro Yamamoto; Yukihiro Sogabe; Shigenori Emi, all of Tsuruga, Japan

[73] Assignee: Toyo Boseki Kabushiki Kaisha, Osaka, Japan

[21] Appl. No.: 249,074

[22] Filed: May 25, 1994

Related U.S. Application Data

[63] Continuation of Ser. No. 972,026, Nov. 6, 1992, abandoned.

[30] Foreign Application Priority Data

Nov. 6, 1991 [JP] Japan .................... 3-319993

[51] Int. Cl.⁶ .................... C12Q 1/40; C12Q 1/54; C12N 1/00; G01N 33/20
[52] U.S. Cl. .................... 435/22; 435/14; 435/15; 435/18; 435/26; 435/4; 435/832; 436/74; 436/63
[58] Field of Search .................... 435/22, 26, 18, 435/4, 14, 15, 832; 436/74, 63

[56] References Cited

U.S. PATENT DOCUMENTS

| | | | |
|---|---|---|---|
| 4,000,042 | 12/1976 | Adams .................... | 435/26 |
| 4,036,697 | 7/1977 | Pierre et al. .................... | 435/26 |
| 4,102,747 | 7/1978 | Driscoll et al. .................... | 435/22 |
| 4,337,309 | 6/1982 | McGeeney .................... | 435/22 |
| 4,427,771 | 1/1984 | Misaki et al. .................... | 435/26 |
| 4,505,756 | 3/1985 | Nix et al. .................... | 435/22 |
| 4,544,631 | 10/1985 | Rauscher et al. .................... | 435/18 |
| 4,794,078 | 12/1988 | Blair .................... | 435/18 |
| 4,932,871 | 6/1990 | Bell et al. .................... | 435/22 |
| 4,987,067 | 1/1991 | Ishimaru et al. .................... | 435/22 |
| 4,990,445 | 2/1991 | Poudrier et al. .................... | 435/22 |
| 5,043,436 | 8/1991 | Ogawa .................... | 435/22 |
| 5,068,182 | 11/1991 | Schmidt et al. .................... | 435/22 |

OTHER PUBLICATIONS

Chung et al, (Abstract), (1987 Nov.), vol. 20(4), p. 327.

Primary Examiner—John Kight
Assistant Examiner—Louise N. Leary
Attorney, Agent, or Firm—Foley & Lardner

[57] ABSTRACT

A method for determining α-amylase activity which involves bringing a sample into contact with an α-glucosidase in the presence of an α-amylase substrate and optically determining a liberated label, the substrate being a maltooligosaccharide composed of at least 3 glucose units, whose reducing terminal glucose is bonded to an optically measurable label at the 1-position by α-glucoside linkage or β-glucoside linkage, and whose non-reducing terminal glucose is modified by a substituent other than glucose, and the α-glucosidase being substantially capable of acting on glucose to which the label is bonded at the 1-position by α-glucoside linkage and on all maltooligosaccharides having 2 to 7 glucose units; and a reagent for determining α-amylase activity comprising the α-glucosidase and said α-amylase substrate. The present invention permits, in the determination of α-amylase activity, efficient auxiliary action of adjuvant enzyme, a determination with good sensitivity, and little reagent blank reaction.

11 Claims, 4 Drawing Sheets

METHOD FOR DETERMINATION OF α-AMYLASE ACTIVITY

This application is a continuation of U.S. patent application Ser. No. 07/972,026 filed Nov. 6, 1992, now abandoned.

BACKGROUND OF THE INVENTION

The present invention relates to a method for the determination of α-amylase activity in body fluid, which is a clinical parameter in the diagnoses of pancreatic diseases and sialadenotropic diseases, and to reagents for the determination of α-amylase activity.

Of the methods for the determination of α-amylase activity, a method using a maltooligosaccharide has been currently in wide use with the spread of autoanalyzers. α-Amylase activity has hitherto been determined by using a maltooligosaccharide having an unmodified non-reducing terminal glucose and α-glucosidase and, if necessary, β-glucosidase as adjuvant enzyme(s) for α-amylase, and determining free glucose, or by optically determining a label liberated from reducing terminal glucose. In these determination methods, an α-glucosidase originated from yeast (the genus Saccharomyces) is often used.

Since this α-glucosidase also acts on maltooligosaccharides whose reducing terminal glucose is bonded to a label, but scarcely acts on maltooligosaccharides having a glucose chain length equal to or longer than that of maltotetraose (G4), it acts very slowly on maltooligosaccharides having a chain length not less than G4 and unmodified non-reducing terminal glucose prior to the action of α-amylase, with the result that the reagent blank reaction occurs satisfactorily less. The α-glucosidase as an adjuvant enzyme needs to immediately decompose the maltooligosaccharide produced by α-amylase.

This α-glucosidase originated from yeast, however, exhibits lowered activity as the glucose chain becomes longer. Concretely speaking, the activity on maltotriose (G3) is poor. Accordingly, it is required to add an excess amount of enzyme for use as an adjuvant enzyme. In addition, the reagent poses problems in terms of stability. When the enzyme is kept in contact with a substrate for a long period of time, the enzyme gradually acts on the substrate, for which reason the reagent containing the enzyme and a substrate need to be used immediately for the determination of α-amylase activity upon preparation thereof.

In recent years, a method using a maltooligosaccharide having a modified non-reducing terminal glucose as a maltooligosaccharide for a substrate has received increased attention. This method is advantageous in that the substrate is not attacked by an adjuvant enzyme before the action of α-amylase, since the non-reducing terminal glucose of the substrate has been modified. Accordingly, reagents are still usable upon long-term storage after preparation of reagents containing the enzyme and the substrate, enabling preparation of a single-vial reagent containing enzyme(s) and substrate(s) for the determination of α-amylase activity.

Nonetheless, this method also poses problems of specificity of α-glucosidase for a substrate, and for a sensitive determination to be conducted by an efficient adjuvant reaction, it is required to add a large excess of α-glucosidase. Such use of a large amount of enzyme can cause economical disadvantages, and other problems such as cloudiness of the reagent and a possible increase of reagent blank reaction due to the enzyme existing in an enzyme standard product.

Further, when a maltooligosaccharide having 7 or more glucose units is used as the substrate, maltooligosaccharides having a glucose chain length equal to or longer than that of maltotetraose (G4) may possibly be produced. It is extremely difficult to decompose such maltooligosaccharides by the α-glucosidase as mentioned above. As a result, labels cannot be liberated upon α-amylase reaction, and there was a case where α-amylase activity values needed to be calculated by multiplying measurement values by stoichiometric coefficients.

In order to solve the problems as mentioned above, U.S. Pat. No. 4,794,078 teaches concurrent use of α-glucosidase and glucoamylase. That is, glucoamylase is allowed to mainly decompose maltooligosaccharides having a glucose chain length equal to or longer than that of maltotriose (G3). According to this method, use of a maltooligosaccharide having a glucose chain length equal to or longer than that of maltoheptaose (G7) as the substrate does not necessitate the aforementioned calculation by multiplying stoichiometric coefficients, since the maltooligosaccharide can be easily decomposed into glucose units, which in turn results in improvement of sensitivity of the determination system. Concomitant decrease of the total enzyme amount can lead to advantages that the method is economical, the reagent does not become cloudy, and that the reagent blank reaction can be inhibited.

While glucoamylase acts well on maltooligosaccharides having a glucose chain length equal to or longer than that of maltotriose (G3) irrespective of the chain length of glucose units, it acts poorly on maltose (G2). In addition, since glucoamylase does not act on reducing terminal glucose having a label bonded thereto, it cannot be used alone as an adjuvant enzyme for α-amylase activity determination.

An object of the present invention is to provide a method for the determination of α-amylase activity, which can solve the problems as mentioned above.

A further object of the present invention is to provide reagents for the determination of α-amylase activity.

SUMMARY OF THE INVENTION

As a result of the intensive studies made by the present inventors, it has now been found that when α-glucosidase, substantially capable of acting on glucose having as wherein a label α-glucoside linked at the 1-position, and on all maltooligosaccharides having 2 to 7 glucose units, is used for the determination of α-amylase activity using maltooligosaccharides having modified non-reducing terminal glucose, an efficient adjuvant reaction can be achieved by the α-glucosidase alone without the concurrent use of glucoamylase, which resulted in the completion of the invention.

In accordance with the present invention, there is provided a method for determining an α-amylase activity which comprises: bringing a sample into contact with an α-glucosidase and, if necessary, a β-glucosidase in the presence of an α-amylase substrate, and optically determining a label released; said substrate being a maltooligosaccharide composed of at least 3 glucose units, whose reducing terminal glucose is linked with an optically measurable label at the 1-position by α-glucoside linkage or β-glucoside linkage and whose non-reducing terminal glucose is modified by a substituent other than glucose, and said α-glucosidase being substantially capable of acting on glucose having said label bonded at the 1-position by α-glucoside linkage and on all maltooligosaccharides composed of 2 to 7 glucose units.

Also, in accordance with the present invention, there is provided a reagent for determining α-amylase activity comprising:
(a) an α-amylase substrate which is a maltooligosaccharide composed of at least 3 glucose units, whose reducing terminal glucose is bonded to an optically measurable label at the 1-position by α-glucoside linkage or β-glucoside linkage, and whose non-reducing terminal glucose is modified by a substituent other than glucose,
(b) an α-glucosidase substantially capable of acting on glucose to which said optically measurable label is bonded at the 1-position by α-glucoside linkage and on all maltooligosaccharides composed of 2 to 7 glucose units, and, if necessary,
(c) a β- glucosidase.

DETAILED DESCRIPTION OF THE INVENTION

Figure 1:
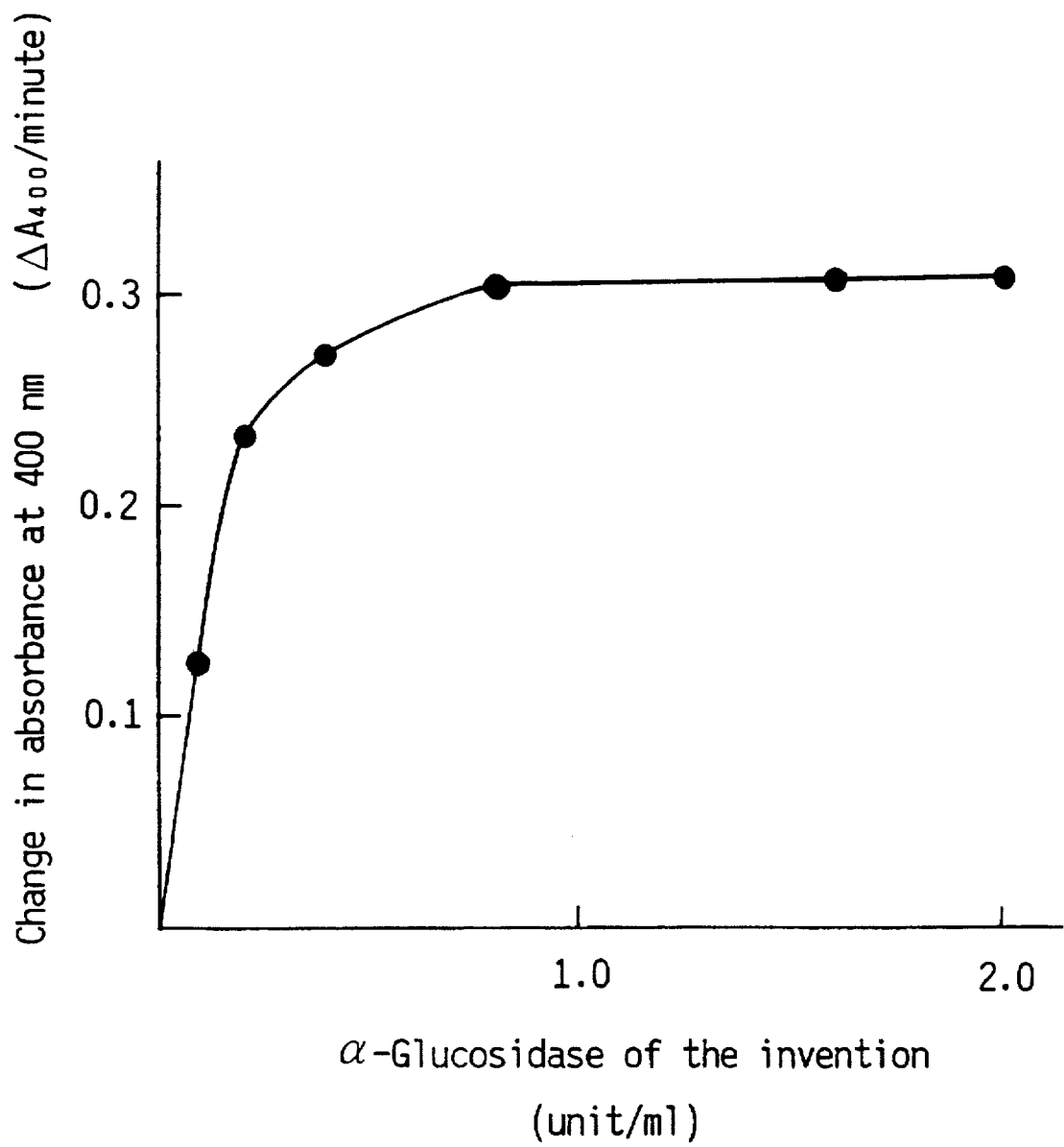
FIG. 1 is a graph showing the relationship between the amount of α-glucosidase added in the reagent in the present invention, and changes in absorbance obtained by using 3-ketobutylidene β-2-chloro-4-nitrophenylmaltopentaoside.

The α-glucosidase to be used in the present invention, namely, the α-glucosidase substantially capable of acting on glucose to which a label is bonded at the 1-position by α-glcoside linkage and on all maltooligosaccharides composed of 2 to 7 glucose units, may be of any origin including animals, plants, microorganisms, and so on. Or, the α-glucosidase may be prepared by genetic engineering. In general, α-glucosidase and glucoamylase are classified by an anomer of glucose produced by cleavage. That is, α-glucose is produced from α-glucosidase and β-glucose is produced from glucoamylase. The α-glucosidases reported are mainly available from the genus Bacillus of a microorganism and from grain from among plants. The α-glucosidase derived from *Bacillus stearothermophilus* is the most preferable. This enzyme is well-suited for the objects of the present invention in that this enzyme acts well on all maltooligosaccharides composed of 2 to 7 glucose units, as well as glucose to which a label is bonded at the 1-position by α-glucoside linkage and labeled maltooligosaccharides, that labels can be liberated, and that this enzyme is extremely stable.

In the present invention, β-glucosidase is co-used with α-glucosidase when a label is bonded to the reducing terminal glucose of a maltooligosaccharide by β-linkage. This β-glucosidase may be of any origin which is exemplified by almonds, etc.

Examples of the maltooligosaccharide composed of at least 3 glucose units which is to be used as the substrate in the present invention are maltotriose, maltotetraose, maltopentaose, maltohexaose, maltoheptaose, maltooctaose, and the like. Any substrates can be used so long as the main decomposition product by α-amylase is a maltooligosaccharide equal to or lower than maltoheptaose (G7).

As the labeled compound to be bonded to the reducing terminal glucose of the maltooligosaccharide by a glucosidic linkage, any compound can be used so long as it can be bonded to the reducing terminal glucose of the maltooligosaccharide by α-linkage or β-linkage, it can be easily cleaved by the action of α-glucosidase or β-glucosidase, and it can be optically determined. Preferred are compounds having a substituted or unsubstituted phenol residue, and the most preferable are 4-nitrophenol, 2-chloro-nitrophenol, and the like. Substrates wherein a label is bonded to the reducing terminal glucose by β-linkage exhibit good solubility, and such substrates are preferable.

As the substituent to modify the non-reducing terminal glucose, any group can be used so long as it can protect the linkage between the substituent and non-reducing terminal glucose and the linkage between non-reducing terminal glucose and adjacent glucose from cleavage by adjuvant enzymes. Examples of the substituent are an ethoxy group, phenoxy group, pyridyloxy group, ethylcarboxyl group, ketopropylidene group, ketobutylidene group, ethylidene group, benzylidene group, β-D-galactopyranosyl group, and the like. Of these, a ketobutylidene group, ethylidene group, benzylidene group and β-D-galactopyranosyl group are preferably used.

The α-amylase activity is, for example, determined as follows:

After mixing a maltooligosaccharide substrate solution with an adjuvant enzyme solution, a sample is added thereto, and the reaction is conducted at about 37° C., followed by determination of change in absorbance per minute.

The present invention is more detailedly and specifically described by means of the following Examples, to which the present invention is not limited.

EXAMPLE 1 AND COMPARATIVE EXAMPLE 1

The following ingredients were dissolved in 6 l of tap water, and the aqueous solution was adjusted to pH 7.0, followed by treatment in an autoclave.

| | |
|---|---|
| Soluble starch | 120 g |
| Peptone | 120 g |
| Beef extract | 3 g |
| Yeast extract | 12 g |
| $K_2HPO_4$ | 18 g |
| $KH_2PO_4$ | 6 g |

The above-mentioned medium in a 10 l jar fermentor was seeded with *Bacillus stearothermophilus* (ATCC 12016 17th edition catalogue, 1989), and subjected to aeration stirring culture at 60° C. for 10 hours, followed by centrifugation to give 80 g of cell. The cells were pulverized by using a Dyno mill, and was purified by ammonium sulfate fractionation, ion-exchange chromatography, and hydrophobic chromatography to give 350 units α-glucosidase standard product.

Using the obtained product, the reactivity to glucose (PNPG), maltose (PNPG2), maltotriose (PNPG3), maltotetraose (PNPG4), maltopentaose (PNPG5), maltohexaose (PNPG6) and maltoheptaose (PNPG7), to each of which a 4-nitrophenyl group had been bonded as a label at the 1-position by α-glucoside linkage, was examined. Separately, reactivity of the marketed α-glucosidase derived from yeast (manufactured by Toyo Boseki Kabushiki Kaisha) was examined in the same manner as above. The reaction velocity was determined by measuring the amount of glucose liberated, and the activity to PNPG was taken as 100. The results are shown in Table 1.

The α-glucosidase activity was calculated as follows:

With 0.5 ml of a substrate solution containing 20 mM 4-nitrophenyl-α-D-glucopyranoside was mixed 1.0 ml of 0.1M phosphate buffer (pH 7.0), and the mixture was pre-heated at 37° C. for 5 minutes. Thereafter, 0.5 ml of an enzyme solution was added thereto and the reaction was conducted at 37° C. for 5 minutes, followed by determination of changes in absorbance per minute at 400 nm. The enzyme activity producing 1 μmol of 4-nitrophenol per minute under the above-mentioned conditions was taken as one unit.

TABLE 1

| Origin Substrate | α-Glucosidase derived from the genus *Bacillus* (Example 1) Reaction velocity | α-Glucosidase derived from yeast (Comparative Example 1) Reaction velocity |
| --- | --- | --- |
| PNPG | 100 | 100 |
| PNPG2 | 253 | 11.2 |
| PNPG3 | 295 | 6.9 |
| PNPG4 | 233 | 1.3 |
| PNPG5 | 137 | 1.0 |
| PNPG6 | 112 | 0 |
| PNPG7 | 93 | 0 |

The α-glucosidase derived from *Bacillus stearothermophilus* showed high reaction velocity in all cases. Particularly when PNPG3 was used, the highest reaction velocity could be obtained, and when the substrates other than PNPG3 were used, sufficiently high reaction velocity could be obtained. On the other hand, the α-glucosidase derived from yeast acted poorly on the maltooligosaccharide having a glucose chain length of G3, and scarcely acted on the maltooligosaccharides having a glucose chain length equal to or longer than G4.

EXAMPLE 2

(1) As the reagent for determining α-amylase activity, the following solutions were prepared.
(A) 4 mM 3-Ketobutylidene β-2-chloro-4-nitrophenylmaltopentaoside dissolved in 0.05 M PIPES buffer (pH 7.0) containing 1 mM calcium chloride
(B) α-Glucosidase derived from *Bacillus stearothermophilus* dissolved in 0.05M PIPES buffer (pH 7.0), in various concentrations of α-glucosidase in the range of from 0 to 2 units per ml, and β-glucosidase, 20 units per ml (2) The α-amylase activity was determined by the following procedure.

After mixing 1.4 ml of solution (A) with 1.4 ml of solution (B), 0.2 ml of an α-amylase standard solution (130 Somogyi units per l, manufactured by The Green Cross Corporation) was added thereto and the reaction was conducted at 37° C. for 3 minutes, followed by determination of the increase in absorbance per minute at 400 nm. The relationship between α-glucosidase concentration and changes in absorbance per minute is shown in FIG. 1. As shown in FIG. 1, there was no difference in the absorbance change when added with α-glucosidase in various amounts of 0.8 unit per ml or more. That is, the α-glucosidase showed complete adjuvant enzyme reaction when added in the reagent for α-amylase activity determination of the present invention in an amount of 0.8 unit per ml or more.

Comparative Example 2

Figure 2:
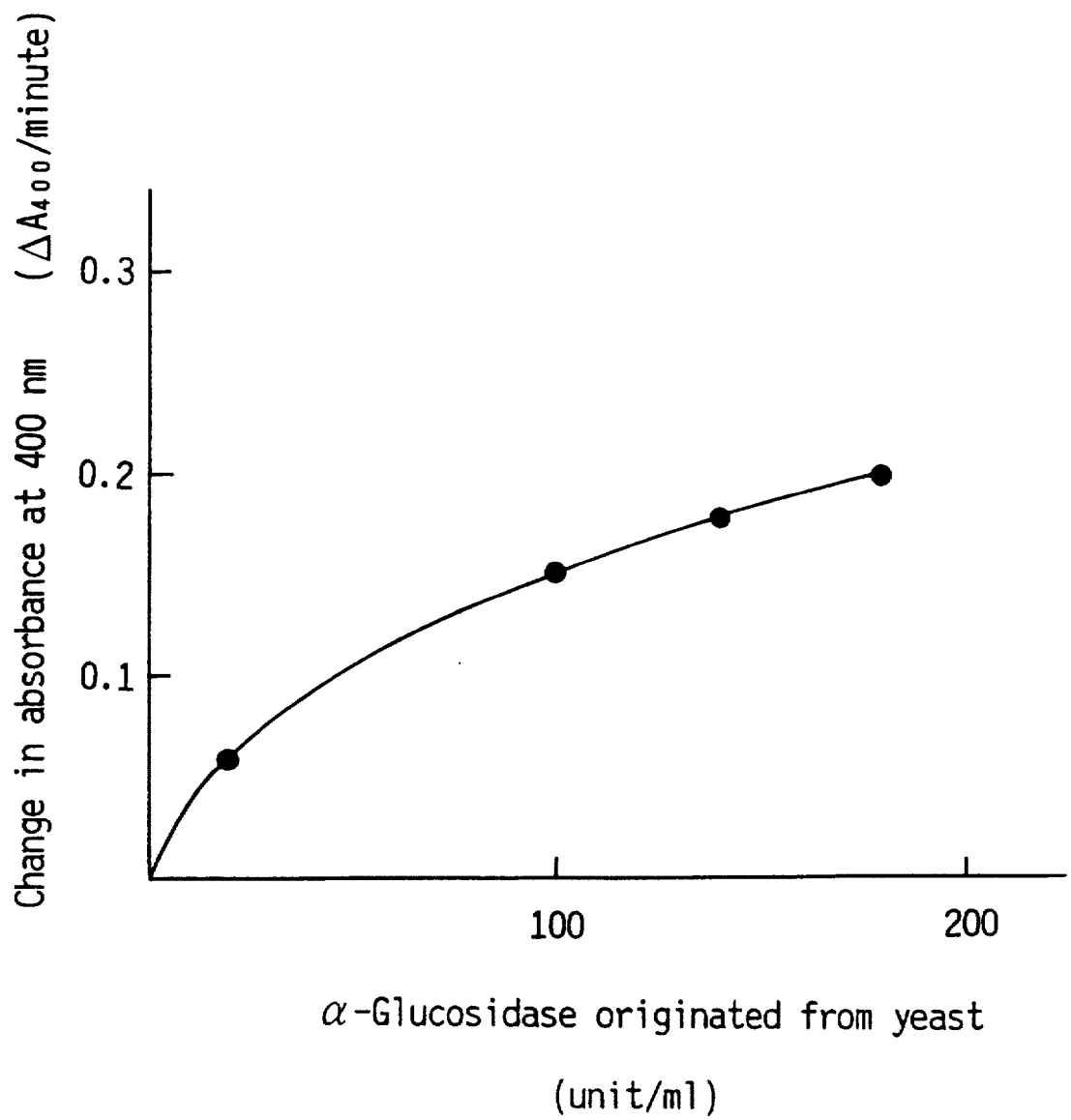
FIG. 2 is a graph showing the relationship between the amount of α-glucosidase originated from yeast, and changes in absorbance obtained by using 3-ketobutylidene β-2-chloro-4-nitrophenylmaltopentaoside.

The procedure of Example 2 was repeated except that the α-glucosidase in the reagent for determining α-amylase activity was changed to a marketed yeast-originated α-glucosidase (0 to 180 units per ml, manufactured by Toyo Boseki Kabushiki Kaisha), to determine the amounts of α-glucosidase necessary (FIG. 2). Even when the yeast-originated α-glucosidase was added in an amount of 180 units per ml, the change in absorbance did not reach the value obtained in Example 2.

EXAMPLE 3

(1) As the reagent for determining α-amylase activity, the following solutions were prepared.
(A) 4 mM 3-Ketobutylidene β-2-chloro-4-nitrophenylmaltopentaoside dissolved in 0.05M PIPES buffer (pH 7.0) containing 1 mM calcium chloride
(B) α-Glucosidase derived from *Bacillus stearothermophilus* dissolved in 0.05M PIPES buffer (pH 7.0), 4 units per ml, and β-glucosidase, 2 units per ml (2) The α-amylase activity was determined by the following procedure.

Figure 3:
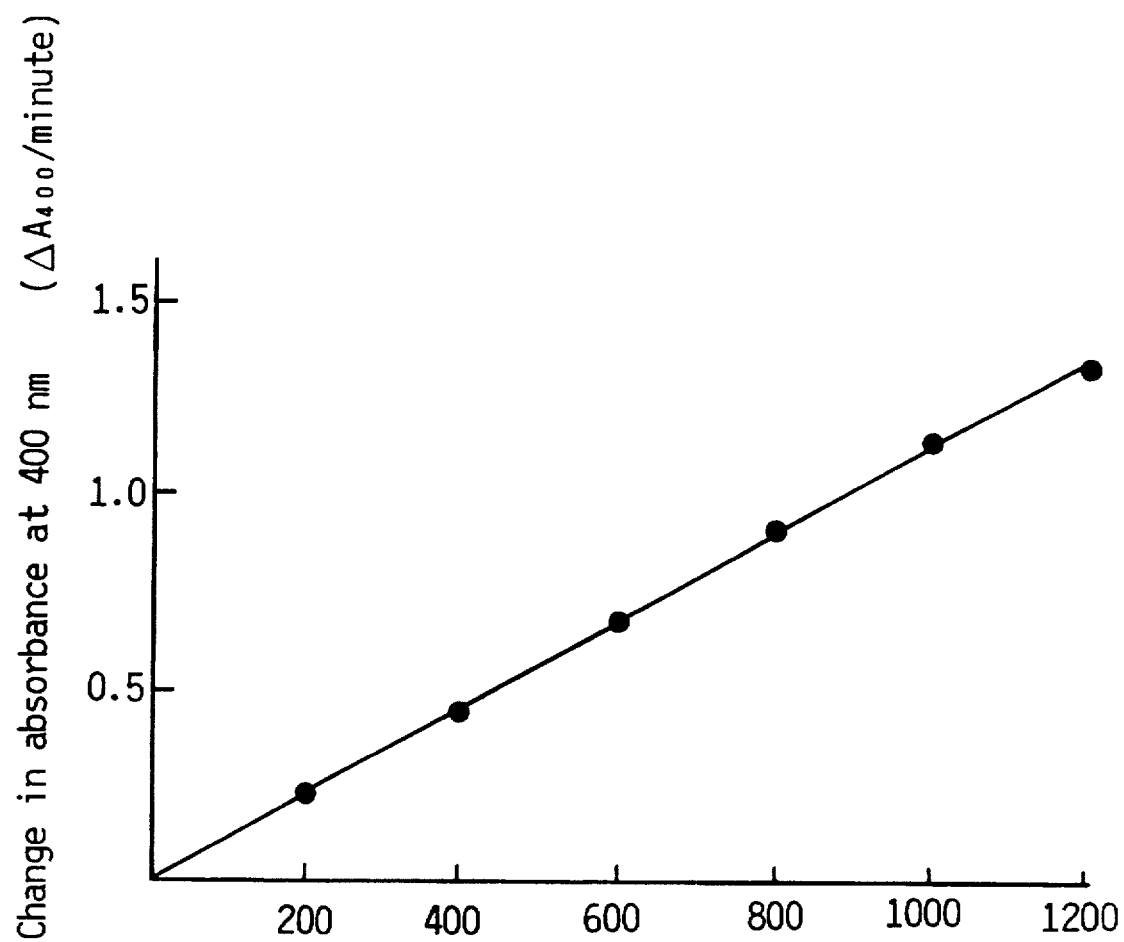
FIG. 3 is a graph showing the linear relationship between α-amylase concentration, and changes in absorbance, when the same substrate was used.

After mixing 1.4 ml of solution (A) with 1.4 ml of solution (B), 0.2 ml of the α-amylase solution diluted to various concentrations in a range of from 0 to 1200 Somogyi units per l was added thereto, and the reaction was conducted at 37° C. for 3 minutes, followed by determination of the increase in absorbance per minute at 400 nm. The relationship between α-glucosidase concentration and absorbance change per minute is shown in FIG. 3. As shown in FIG. 3, a linear relationship could be observed between the α-amylase concentration and the change in absorbance.

EXAMPLE 4

(1) As the reagent for determining α-amylase activity, the following solutions were prepared.
(A) 6 mM Ethylidene-α-4-nitrophenylmaltoheptaoside dissolved in 0.1M PIPES buffer (pH 7.0) containing 1 mM calcium chloride
(B) α-Glucosidase derived from *Bacillus stearothermophilus* dissolved in 0.1M PIPES buffer (pt 7.0), in various concentrations of α-glucosidase in the range of from 0 to 8 units per ml (2) The α-amylase activity was determined by the following procedure.

Figure 4:
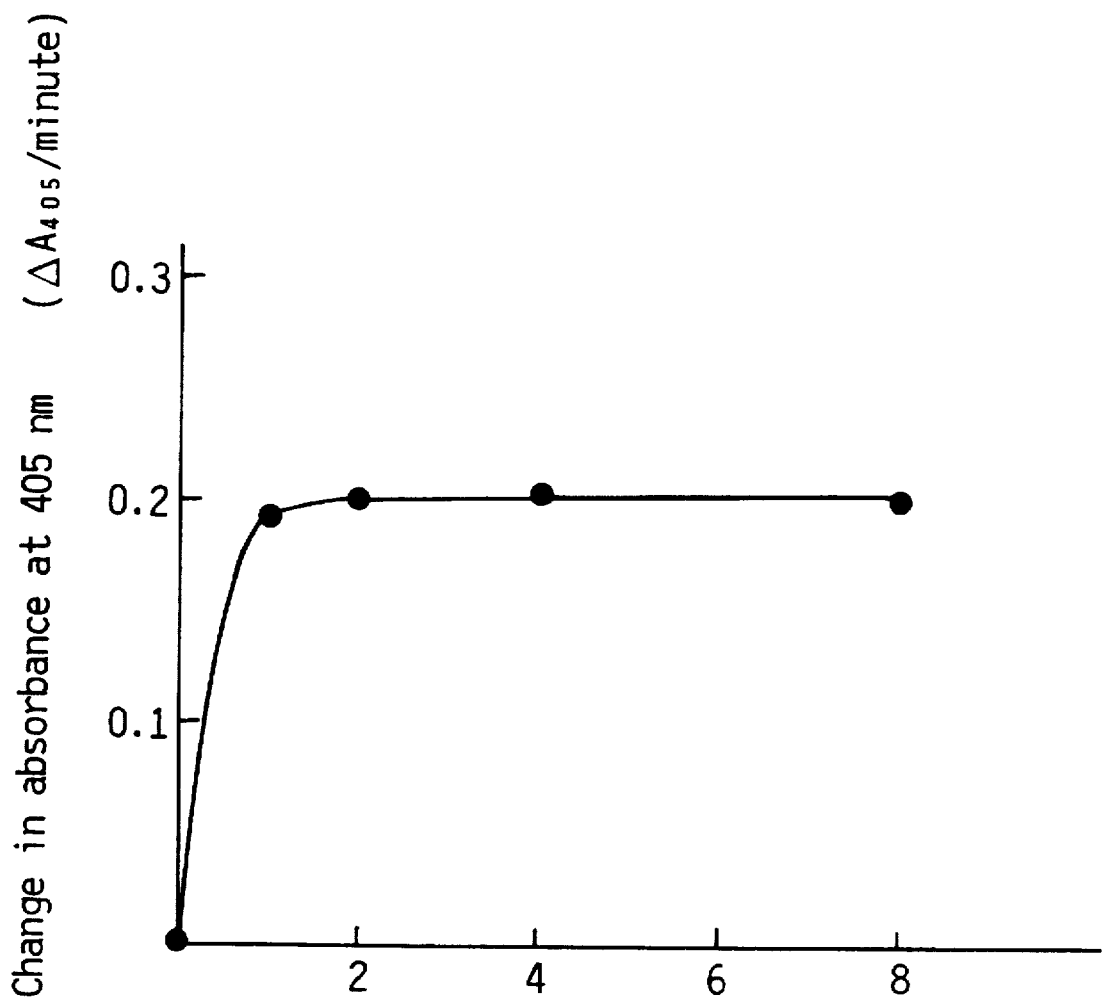
FIG. 4 is a graph showing the relationship between the amount of α-glucosidase used in the present invention, and changes in absorbance obtained by using ethylidene-α-4-nitrophenylmaltoheptaoside.

After mixing 1.4 ml of solution (A) with 1.4 ml of solution (B), 0.2 ml of an α-amylase standard solution (130 Somogyi units per l, manufactured by The Green Cross Corporation) was added thereto, and the reaction was conducted at 37° C. for 3 minutes, followed by determination of the increase in absorbance per minute at 405 nm. The relationship between the α-glucosidase concentration and absorbance change per minute is shown in FIG. 4. As shown in FIG. 4, there was no difference in the absorbance change when added with α-glucosidase in various amounts of 2 units per ml or more. That is, the α-glucosidase showed complete adjuvant enzyme reaction when added in the reagent for α-amylase activity determination of the present invention in an amount of 2 units per ml.

Accordingly, the present invention permits, in the determination of α-amylase activity, efficient adjuvant enzyme reaction, a determination with good sensitivity, and little reagent blank reaction, by using the α-glucosidase capable of acting efficiently on the glucose to which a label is bonded at the 1-position by α-glucoside linkage, and on all maltooligosaccharides composed of 2 to 7 glucose units.

What we claim is:

1. A method for determining α-amylase activity which comprises:

bringing a sample into contact with an α-glucosidase in the presence of an α-amylase substrate, and optically determining a liberated label;

said substrate being a maltooligosaccharide composed of at least 3 glucose units, whose reducing terminal glucose is bonded to an optically measurable label at the 1-position by α-glucoside linkage or β-glucoside linkage, and whose non-reducing terminal glucose is modified by a substituent other than glucose, and said α-glucosidase being capable of acting on glucose to which said label is bonded at the 1-position by α-glucoside linkage and on all maltooligosaccharides composed of 2 to 7 glucose units.

2. The method of claim 1, wherein a β-glucosidase is used together with said α-glucosidase.

3. The method of claim 1, wherein said α-glucosidase is derived from a strain belonging to the genus Bacillus.

4. The method of claim 1, wherein said α-glucosidase is derived from a strain belonging to *Bacillus stearothermophilus*.

5. The method of claim 1, wherein said label is a substituted or unsubstituted phenol residue.

6. The method of claim 1, wherein the α-glucosidase is used in an amount of 2 units per ml or more.

7. A reagent for determining α-amylase activity comprising:

(a) an α-amylase substrate which is a maltooligosaccharide composed of at least 3 glucose units, whose reducing terminal glucose is bonded to an optically measurable label at the 1-position by α-glucoside linkage, or β-glucoside linkage, and whose non-reducing terminal glucose is modified by a substituent other than glucose, and (b) an α-glucosidase capable of acting on glucose to which said label is bonded at the 1-position by α-glucoside linkage, and on all maltooligosaccharides composed of 2 to 7 glucose units.

8. The reagent of claim 7, which further comprises a β-glucosidase.

9. The reagent of claim 7, wherein said α-glucosidase is derived from a strain belonging to the genus Bacillus.

10. The reagent of claim 7, wherein said α-glucosidase is derived from a strain belonging to *Bacillus stearothermophilus*.

11. The reagent of claim 7, wherein said label is a substituted or unsubstituted phenol residue.

* * * * *